(12) United States Patent
Pan

(10) Patent No.: US 11,468,979 B2
(45) Date of Patent: Oct. 11, 2022

(54) INTEGRATED SYSTEM FOR PICTURE ARCHIVING AND COMMUNICATION SYSTEM AND COMPUTER AIDED DIAGNOSIS

(71) Applicant: EBM TECHNOLOGIES INCORPORATED, Taipei (TW)

(72) Inventor: William Pan, Taipei (TW)

(73) Assignee: EBM TECHNOLOGIES INCORPORATED, Taipei (TW)

( * ) Notice: Subject to any disclaimer, the term of this patent is extended or adjusted under 35 U.S.C. 154(b) by 167 days.

(21) Appl. No.: 16/816,302

(22) Filed: Mar. 12, 2020

(65) Prior Publication Data

US 2021/0249117 A1 Aug. 12, 2021

(30) Foreign Application Priority Data

Feb. 6, 2020 (TW) ................... 109103713

(51) Int. Cl.
*G16H 30/20* (2018.01)
*G16H 50/20* (2018.01)
(Continued)

(52) U.S. Cl.
CPC ......... *G16H 30/20* (2018.01); *G06F 16/9535* (2019.01); *G06T 7/0012* (2013.01); *G16H 15/00* (2018.01); *G16H 30/40* (2018.01); *G16H 50/20* (2018.01); *G16H 80/00* (2018.01); *G06T 2207/10081* (2013.01); *G06T 2207/10088* (2013.01); *G06T 2207/10116* (2013.01); *G06T 2207/10132* (2013.01); *G06T 2207/30096* (2013.01)

(58) Field of Classification Search
CPC ......... G16H 15/00; G16H 50/20; G16H 30/40
See application file for complete search history.

(56) References Cited

U.S. PATENT DOCUMENTS 9,036,510 B1 * 5/2015 Zhou .................. H04W 4/10
370/263
10,096,107 B2 10/2018 Ghesu
(Continued)

FOREIGN PATENT DOCUMENTS

| CN | 106372390 B | 4/2019 |
| JP | 2020-500377 | 1/2020 |
| TW | 201921376 A | 6/2019 |

*Primary Examiner* — Jonathan Ng
(74) *Attorney, Agent, or Firm* — Winston Hsu

(57) ABSTRACT

The invention provides an integrated system capable of integrating Picture Archiving and Communication System (PACS) and Computer Aided Diagnosis (CAD), which allows users to login account, retrieve/preview/download database, process an image, configure an image, input operation instructions, and execute synchronization/conference function, etc. through a user interface provided by an integrated application, a remote browsing gateway or a remote browsing webpage. Through the instinctive and user-friendly interface, the users may increase their willingness to use PACS and CAD. In addition, the integrated system combines the functions of PACS and CAD systems and may be applied to cancer or tumor screening to promote the advancement of medical diagnosis and highlight its possible contributions and potential value of PACS and CAD systems.

7 Claims, 2 Drawing Sheets

(51) Int. Cl.
*G16H 15/00* (2018.01)
*G16H 30/40* (2018.01)
*G16H 80/00* (2018.01)
*G06T 7/00* (2017.01)
*G06F 16/9535* (2019.01)

(56) References Cited

U.S. PATENT DOCUMENTS

| | | | | |
|---|---|---|---|---|
| 2006/0135865 | A1* | 6/2006 | Bharara | G06T 19/00 |
| | | | | 600/407 |
| 2009/0100096 | A1* | 4/2009 | Erlichson | H04L 67/02 |
| 2011/0238618 | A1* | 9/2011 | Valdiserri | G16H 30/40 |
| | | | | 707/E17.019 |
| 2013/0325493 | A1* | 12/2013 | Wong | G16Z 99/00 |
| | | | | 705/2 |
| 2014/0033126 | A1* | 1/2014 | Kreeger | G06T 11/003 |
| | | | | 715/833 |
| 2014/0365242 | A1* | 12/2014 | Neff | G16H 10/60 |
| | | | | 707/756 |
| 2015/0125832 | A1* | 5/2015 | Tran | G09B 5/00 |
| | | | | 434/127 |
| 2017/0076046 | A1* | 3/2017 | Barnes | G16H 30/20 |
| 2017/0200270 | A1* | 7/2017 | Reicher | A61B 5/7271 |
| 2018/0144465 | A1* | 5/2018 | Hsieh | G06N 3/04 |
| 2019/0164285 | A1* | 5/2019 | Nye | G06T 7/70 |

* cited by examiner

INTEGRATED SYSTEM FOR PICTURE ARCHIVING AND COMMUNICATION SYSTEM AND COMPUTER AIDED DIAGNOSIS

BACKGROUND OF THE INVENTION

1. Field of the Invention

The invention relates to an integrated system, and more particularly, to an integrated system for picture archiving and communication system and computer aided diagnosis.

2. Description of the Prior Art

The picture archiving and communication system (PACS) is a computer or network system specifically used for storing, obtaining, transmitting, and displaying medical images. The PACS may obtain images from a variety of medical imaging equipment, such as: Ultrasound Image, Magnetic Resonance Imaging (MRI), Positron Tomography (PT), Computed Tomography (CT), Mammography (MG), Digital Radiography (DR), Computed Radiography (CR), and X-ray plain film (PF).

A Digital Imaging and Communications in Medicine (DICOM) protocol used by the PACS is a set of common standard protocols specifically used for processing, storing, printing, and transmitting medical images. The set of common standard protocols regulate definitions of DICOM format files and network communication protocols. The DICOM is based on Transmission Control Protocol (TCP) and Internet Protocol (IP) (TCP/IP protocol) to communicate between a host (e.g., a server) and multiple terminals (e.g., medical instruments, workstations). For example, a workstation and a medical instrument capable of receiving DICOM files may exchange the DICOM files (which include medical images and data of patients, etc.) according to the TCP/IP protocol.

On the other hand, the computer aided diagnosis (CAD) is a system used to assist physicians in interpreting medical images. For example, artificial intelligence (AI) models established by the CAD can perform AI image identification to mark suspected tumor tissues or atypical cell tissues in medical images to provide medical professionals for diagnosis.

However, because the PACS and the CAD are two independent systems, users must learn how to use the two systems separately. This leads to a low using willingness to use the PACS and the CAD, and wastes possible contributions and potential values of the PACS and the CAD for medical diagnosis.

Therefore, in order to make full use of functions of the PACS and the CAD to promote an advancement of medical diagnosis, it is necessary to provide an integrated system that can integrate the PACS and the CAD.

SUMMARY OF THE INVENTION

It is therefore a primary objective of the present invention to provide an integrated system for integrating a medical picture archiving system and an aided diagnosis, so as to make progress of medical diagnosis.

The present invention discloses an integrated system, for integrating a picture archiving and communication system (PACS) and a computer aided diagnosis (CAD), comprising: a PACS database, for storing a Digital Imaging and Communications in Medicine (DICOM) image, a datum of patients, and an intranet user account; a CAD database, for storing a CAD file corresponding to the DICOM image and an artificial intelligence (AI) image recognition model parameter; an integrated interface, coupled to the CAD database, for executing an AI image recognition model according to a screening requirement, the CAD file, and the AI image recognition model parameter to generate a screening result corresponding to the screening requirement; an intranet mobile device, for executing an integrated application to provide an intranet user interface to an intranet user corresponding to the intranet user account, wherein the intranet user inputs at least one of a search condition, a service requirement and the screening requirement through the intranet user interface, and the integrated application generates search parameters according to the search condition; and a PACS server, coupled to the PACS database and the integrated interface, and connected to the intranet mobile device. The PACS server is used for: transferring the screening requirement to the integrated interface, and returning the screening result generated by the integrated interface to the intranet mobile device; reading the DICOM image corresponding to the search parameters from the PACS database according to the search parameters; and saving, obtaining, transmitting and displaying at least one of the DICOM image, the datum of patients and the intranet user account from the PACS database according to the service requirement.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
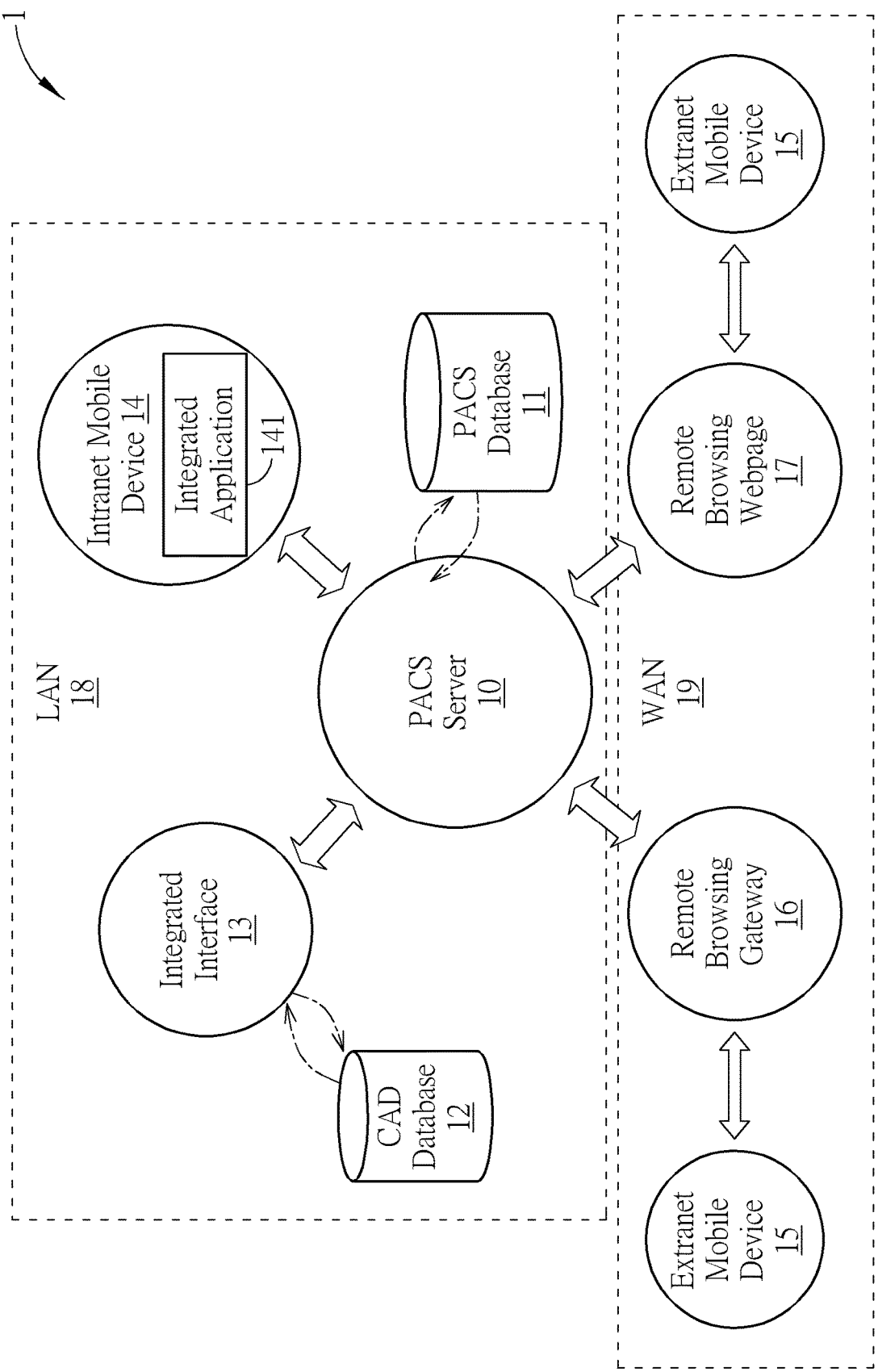
FIG. 1 is a schematic diagram of an integrated system according to an embodiment of the present invention.

FIG. 1 is a schematic diagram of an integrated system 1 according to an embodiment of the present invention. The integrated system 1 is applicable to medical research institutions, medical institutions and care institutions, etc., and is used for integrating a Picture Archiving and Communication System (PACS) and a Computer Aided Diagnosis (CAD), which allows relevant medical personnel to read, store and transmit Digital Imaging and Communications in Medicine (DICOM) formats and Mammography Hanging protocols (MAMMO) used in a PACS architecture through the integrated system 1, converts medical images, and then inputs the converted medical images to the CAD for related medical diagnosis.

As shown in FIG. 1, the integrated system 1 comprises a PACS server 10, a PACS database 11, a CAD database 12, an integrated interface 13, at least one intranet mobile device 14, at least one extranet mobile device 15, a remote browsing gateway 16, and a remote browsing webpage 17. The PACS database 11, coupled to the PACS server 10, is used for storing medical images in DICOM and MAMMO formats used in the PACS architecture, wherein the PACS server 10 may directly access data stored in the PACS database 11. The CAD database 12, coupled to the integrated interface 13, is used for storing the converted medical images, wherein the integrated interface 13 may directly access the data of the CAD database 12, and the PACS server 10 may indirectly access the data of the CAD database 12 through the integrated interface 13. The PACS server 10 may connect to the integrated interface 13, the intranet mobile device 14, the extranet mobile device 15, the remote browsing gateway 16 and the remote browsing webpage 17 through wired or wireless communication.

In this embodiment, the integrated system 1 is established based on a client-server model with a local area network (LAN) 18 and a wide area network (WAN) 19, wherein the intranet mobile device 14 and the extranet mobile device 15 are clients, and the PACS server 10 may provide corresponding services according to the services issued by the clients. The intranet mobile device 14 and the extranet mobile device 15 may be electronic devices (e.g., tablets, smart phones, notebook computers, desktop computers, etc.). Users (e.g., doctors, nurses, caregivers and other related medical practitioners) may operate an user interface (UI) provided by an integrated application 141, the remote browsing gateway 16 or the remote browsing webpage 17 in the electronic devices to send service requests to the PACS server 10. The PACS server 10 is used to implement services that may be provided by a PACS system (such as storing, obtaining, transmitting, and displaying DICOM file objects, where the DICOM file objects contain medical images and patient data).

For example, on the premise that the intranet mobile device 14 installs the integrated application 141, when the intranet mobile device 14 is connected to the PACS server 10 via the LAN 18 in a medical institution, the services may be issued to the PACS server 10 through an intranet user interface provided by the integrated application 141. Specifically, intranet users may enter search conditions through the intranet user interface provided by the integrated application 141, so that the integrated application 141 may determine related search parameters based on the search conditions, and convert the related search parameters into network transmission packets for transmission to the PACS server 10. Then, the PACS server 10 may receive the network transmission packets to read the related search parameters and perform calculations according to the related search parameters, or control the integrated interface 13 to perform calculations to obtain corresponding calculation results (such as at least one medical image and related data sets). Furthermore, the PACS server 10 may compress the calculation results and convert them into network transmission packets for transmission back to the intranet mobile device 14. Finally, the integrated application 141 may control the intranet mobile device 14 to display at least one medical image according to the calculation results. In one embodiment, the network transmission packets are generated according to the TCP/IP protocol. In this way, all the intranet mobile devices 14 that join the LAN 18 in the medical institution may use the integrated system through the integrated application 141 to ensure consistent operation. In addition, the closed LAN 18 also helps reduce the risk of leakage of medical images to maintain patient privacy.

On the other hand, under the premise that the extranet mobile device 15 does not install the integrated application 141, when the extranet mobile device 15 is connected to the LAN 18 via the WAN 19, the services may be issued to the PACS server 10 through an extranet user interface provided by the remote browsing gateway 16 or the remote browsing webpage 17. Specifically, taking the remote browsing webpage 17 as an example, users may enter search conditions through the extranet user interface provided by the remote browsing webpage 17, so that the remote browsing webpage 17 may judge related parameters according to the search conditions, and convert the related parameters into network transmission packets for transmission to the PACS server 10. Then, the PACS server 10 may receive the network transmission packets to read the related parameters and perform calculations according to the related parameters, or control the integrated interface 13 to perform calculations to obtain corresponding calculation results (such as at least one medical image). Furthermore, the PACS server 10 may compress the calculation results and convert them into network transmission packets for transmission back to the extranet mobile device 15. Finally, the remote browsing webpage 17 may control the extranet mobile device 15 to display at least one medical image to the users. In this way, since the extranet mobile device 15 may be connected to the LAN 18 through the remote browsing gateway 16 or the remote browsing webpage 17, the services of the integrated system 1 are not limited to the intranet mobile device 14, so that the extranet users may perform remote medical images review and search to achieve remote medical diagnosis.

Note that, the integrated system 1 may perform multiple operation functions, comprising database search, preview, download, image processing and image configuration functions for a single user, and synchronous functions and conference functions for multiple users, but not limited thereto. In an embodiment, the image processing functions comprise rotation, mirror flip, screenshots, play multiple images continuously, pause image playback, view previous image, view next image, automatically read ambient light source and display grayscale correction, etc., but not limited thereto. Wherein, the purpose of automatically read ambient light source and display grayscale correction operations is to make the DICOM medical images displayed by a mobile device to comply with a DICOM grayscale curve to obtain a DICOM display certification of the Food and Drug Administration (FDA), and the mobile device obtaining the DICOM display certification also helps improving the accuracy of medical image diagnosis. In one embodiment, the image processing function is based on technologies such as ActiveX Control™ and DirectX™ to improve performance of image processing, so that mobile devices may more smoothly display high-quality static or dynamic images.

In one embodiment, the image configuration functions comprise setting multiple images to display at a same time, setting a flat configuration to display multiple images at a same time, measuring a length of an area of interest in images, and viewing medical images in MAMMO format by using a slide mode, but not limited thereto. Further, each user who uses the synchronous function and the conference function may also use the database search, preview, download, image processing and image configuration functions.

In one embodiment, while using the synchronous function, when a mobile device (which may be the intranet mobile device 14 or the extranet mobile device 15) requires image synchronization with another mobile device, the integrated application 141, the remote browsing gateway 16 or the remote browsing webpage 17 may send a network transmission packet containing a synchronous request to the PACS server 10. The PACS server 10 transmits a corresponding synchronous device name (for example, Application Entity Title (AET)) to another mobile device according to the synchronous request. When the PACS server 10 obtains a synchronous confirmation of another mobile device, the PACS server 10 may transmit the same network transmission packet (such as the same medical image and the patient data) to the both mobile devices for synchronous display. In one embodiment, intranet users or extranet users may set one of the mobile devices to have a host identity and set the other mobile device to have a guest identity.

Specifically, the DICOM standard establishes a C-ECHO service, also known as a verification service, for verifying whether the devices at both ends of the DICOM files to be transmitted can communicate smoothly. For example, when the PACS server 10 intends to send a file to a certain mobile device, the PACS server 10 will first send a C-ECHO message to the mobile device to test whether the mobile device is successfully connected. If the connection is successfully set, then the PACS server 10 will record relevant parameters of the confirmed connection and send the file. If other mobile devices intend to connect to the PACS server 10, the other mobile devices will send their application entity title (AET), port number, Internet protocol address (IP Address), etc. to the PACS server 10. Then, the PACS server 10 sends C-ECHO messages to the other mobile devices according to the application entity title, the port number and the Internet protocol address. After confirming the successful connection, the files can be sent. In addition, the DICOM standard also establishes a C-STORE service, also known as a storage service, for storing the DICOM files in the PACS (for example, the PACS database 11). When mobile devices or medical image devices are successfully connected to the PACS server 10, the mobile devices or the medical image devices may send a C-STORE request to the PACS server 10. The PACS server 10 will store the DICOM files in the PACS database 11 according to the C-STORE request, and return a C-STORE response to the mobile devices or the medical image devices. Alternatively, the PACS server 10 may use a Query/Retrieve service to obtain DICOM files or other data from mobile devices or medical image devices.

In one embodiment, while using the conference function, when a certain mobile device (which may be the intranet mobile device 14 or the extranet mobile device 15) requires a conference with another mobile device, the integrated application 141, the remote browsing gateway 16 or the remote browsing webpage 17 may send a network transmission packet containing a conference device name (for example, the Application Entity Title (AET)) corresponding to a conference request to the PACS server 10. The PACS server 10 transmits the conference request to another mobile device accordingly. When the PACS server 10 obtains a conference confirmation of another mobile device, the PACS server 10 may transmit the same medical image, the patient data and the operation instructions to the both mobile devices for synchronous display. For example, when a mobile device with a host identity performs image processing operations (such as manual drawing, zooming in or out of an image, and adjusting positions of a window, etc.), the PACS server 10 may transmit operation instructions corresponding to the image processing function to a mobile device with a guest identity, so as to allow the mobile device with the host identity and the mobile device with the guest identity to display same screens.

In one embodiment, the integrated interface 13 may comprise an artificial intelligence (AI) image recognition model for implementing a computer aided diagnosis (CAD). Since image formats supported by the AI image recognition model may be DICOM and MAMMO image formats not used by the PACS, the integrated interface 13 must first convert DICOM and MAMMO images into an AI image (AI image formats are, for example, Joint Photographic Experts Group (JPG) formats or Portable Network Graphics (PNG) formats), and then execute an AI image recognition. Therefore, in the case of integrating the PACS and the CAD, the integrated system 1 may be applied to cancer or tumor screening requirements. For example, when a user sends a cancer or tumor screening request, the PACS server 10 may read multiple DICOM medical images (including medical images of suspected and confirmed malignant tumors and benign tumor tissues) from the PACS database 11 and the DICOM medical images to be interpreted to the integrated interface 13. The integrated interface 13 converts the received DICOM medical images into JPG or PNG images and stores the JPG or PNG images in the CAD database 12. The integrated interface 13 inputs the stored JPG or PNG images to the AI image recognition model and generates screening results to the PACS server 10. The screening results are, for example, information such as an area of interest and a size of the area of interest in the medical images (for example, an area that is suspected to be tumor tissues and a corresponding size). In this way, the PACS server 10 may return the area of interest and the corresponding size that are suspected to be tumor tissues to the mobile device for diagnosis by the physician.

Figure 2:
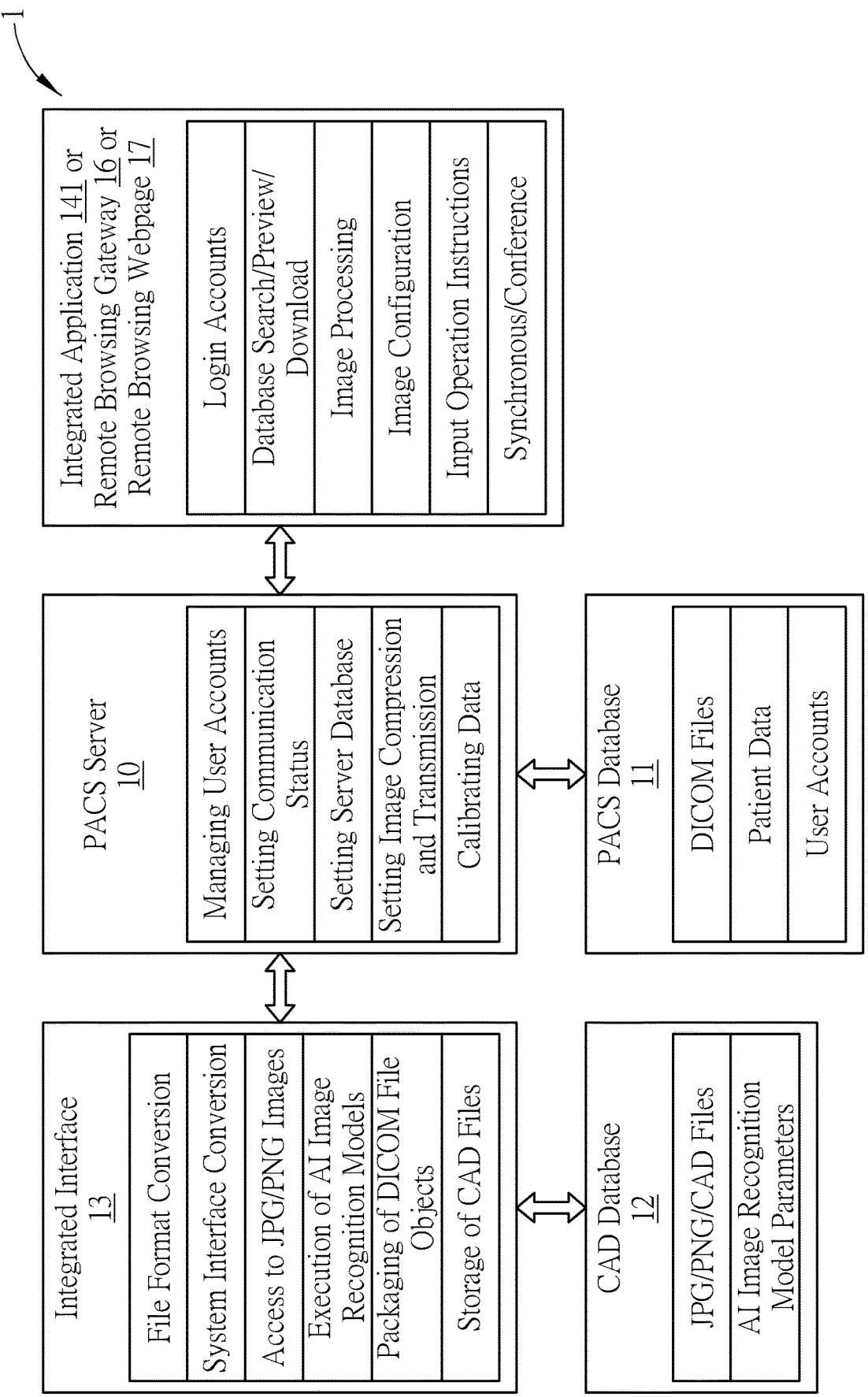
FIG. 2 is a system function architecture diagram of an integrated system according to an embodiment of the present invention.

The system function architecture of the integrated system 1 may be summarized as FIG. 2. As shown in FIG. 2, the functions of the PACS server 10 may at least include: managing user accounts, setting communication status, setting the PACS database, setting image compression and transmission, and calibrating data. The functions of the PACS database 11 may at least include: storage of DICOM files, patient and user accounts. The functions of the integrated interface 13 may at least include: file format conversion, system interface conversion, access to converted images, execution of AI image recognition models, packaging of DICOM file objects, and storage of CAD files. The functions of the CAD database 12 may at least include: storing the converted JPG/PNG image files and AI image recognition model parameters. The functions of the integrated application 141, the remote browsing gateway 16 or the remote browsing webpage 17 may at least include: providing user interfaces to login accounts, database search/preview/download, image processing (including rotation, mirror flip, screenshots, play multiple images continuously, pause image playback, view previous image, view next image, automatically read ambient light source and display grayscale correction, manual drawing, zoom in or out of images, and adjust the position of the window), image configuration (including set multiple images to display at a same time, set a flat configuration to display multiple images at a same time, measure a length of an area of interest in images, and view images by using a slide mode), input operation instructions, and execute synchronous/conference functions. However, it is not limited therein, a person having ordinary knowledge in the art may expand additional functions of the integrated system 1 according to actual application requirements.

In summary, the present invention provides the integrated system 1 capable of integrating the PACS and the CAD, allowing users to use the user interfaces provided by the integrated application 141, the remote browsing gateway 16 or the remote browsing webpage 17 to login accounts, database search/preview/download, image processing, image configuration, input operation instructions, execute synchronous/conference functions, etc. Through intuitive and user-friendly operation interfaces, users may increase their willingness to use the PACS and the CAD. In addition, the integrated system 1 combines the functions of PACS and CAD systems and may be applied to cancer or tumor screening to promote the advancement of medical diagnosis and highlight the possible contributions and potential value of the PACS and the CAD.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An integrated system, for integrating a picture archiving and communication system (PACS) and a computer aided diagnosis (CAD), comprising:
   a PACS database, for storing a Digital Imaging and Communications in Medicine (DICOM) image, a datum of patients, and an intranet user account;
   a CAD database, for storing a CAD file corresponding to the DICOM image and an artificial intelligence (AI) image recognition model parameter;
   an integrated interface, coupled to the CAD database, for executing an AI image recognition model according to a screening requirement, the CAD file, and the AI image recognition model parameter to generate a screening result corresponding to the screening requirement;
   an intranet mobile device, for executing an integrated application to provide an intranet user interface to an intranet user corresponding to the intranet user account, wherein the intranet user inputs at least one of a search condition, a service requirement and the screening requirement through the intranet user interface, and the integrated application generates search parameters according to the search condition, wherein the service requirement comprises a synchronous request or a conference request; and
   a PACS server, coupled to the PACS database and the integrated interface, and connected to the intranet mobile device, for:
      transferring the screening requirement to the integrated interface, and returning the screening result generated by the integrated interface to the intranet mobile device;
      reading the DICOM image corresponding to the search parameters from the PACS database according to the search parameters; and
      saving, obtaining, transmitting and displaying at least one of the DICOM image, the datum of patients and the intranet user account from the PACS database according to the service requirement,
      wherein when a first mobile device of the integrated system sends the synchronous request or the conference request to the PACS server through the integrated application, a remote browsing gateway, or a remote browsing webpage:
         the PACS server transmits a synchronous device name corresponding to the synchronous request or a conference device name corresponding to the conference request to a second mobile device; and
         under a condition that the PACS server obtains a synchronous confirmation or a conference confirmation of the second mobile device, the PACS server transmits the same network transmission packets to the first mobile device and the second mobile device,
      wherein, in a case that the PACS server obtains the synchronous confirmation of the second mobile device, when the first mobile device executes image processing function, the PACS server transmits an operation instruction corresponding to the image processing function to the second mobile device for image synchronization.

2. The integrated system of claim 1, wherein the intranet mobile device connects to the PACS server through a local area network, and the PACS server is utilized for receiving and transmitting the screening requirement, the screening result, the service requirement, the DICOM image, the datum of patients and network transmission packets corresponding to the intranet user account according to the Transmission Control Protocol (TCP) and the Internet Protocol (IP).

3. The integrated system of claim 1, wherein the PACS database is utilized for saving an extranet user account, and the integrated system further comprises:
   an extranet mobile device, connected to the PACS server, for providing an extranet user interface by a remote browsing gateway or a remote browsing webpage to an extranet user corresponding to the extranet user account, wherein the extranet user inputs at least one of the search condition, the service requirement and the screening requirement through the extranet user interface, and the remote browsing gateway or the remote browsing webpage generates the search parameters to the PACS server according to the search condition.

4. The integrated system of claim 3, wherein the extranet mobile device connects to the PACS server through a wide area network, and the PACS server is utilized for receiving and transmitting the screening requirement, the screening result, the service requirement, the DICOM image, the datum of patients and network transmission packets corresponding to the intranet user account according to the TCP/IP.

5. The integrated system of claim 1, wherein
   the service requirement further comprises: database search, preview DICOM file, download DICOM file, the image processing function and image configuration function;
   the image processing function comprises: rotation, mirror flip, screenshots, play multiple images continuously, pause image playback, view previous image, view next image, automatically read ambient light source and display grayscale correction; and
   the image configuration function comprises: set multiple images to display at a same time, set a flat configuration to display multiple images at a same time, measure a length of an area of interest in images, and view images by using a slide mode.

6. The integrated system of claim 1, wherein the image processing function further comprises operations of manual drawing, zooming in or out of an image, and adjusting a position of a window, and when the first mobile device executes the image processing function, the PACS server transmits the operation instruction corresponding to the image processing function to the second mobile device.

7. The integrated system of claim 1, wherein the integrated interface is utilized for:
   receiving the DICOM image corresponding to the screening requirement from the PACS server;
   converting the DICOM image into an AI image and saving the AI image to the CAD database, wherein a format of the AI image includes the Joint Photographic Experts Group (JPG) format or the Portable Network Graphics (PNG) format; and
   inputting the AI image to the AI image recognition model to generate the screening result corresponding to the screening requirement to the PACS server, wherein the screening result includes information indicating an area of interest and a size of the area of interest in the DICOM image.

* * * * *